(12) United States Patent
Gauthier

(10) Patent No.: US 11,679,286 B2
(45) Date of Patent: Jun. 20, 2023

(54) OXYGEN SENSOR CALIBRATION FOR REBREATHER

(71) Applicant: Tesseron Ltd., Key Largo, FL (US)

(72) Inventor: Forrest P. Gauthier, Homestead, FL (US)

(73) Assignee: Tesseron Ltd., Key Largo, FL (US)

( * ) Notice: Subject to any disclaimer, the term of this patent is extended or adjusted under 35 U.S.C. 154(b) by 915 days.

(21) Appl. No.: 16/409,253

(22) Filed: May 10, 2019

(65) Prior Publication Data
US 2019/0358472 A1 Nov. 28, 2019

Related U.S. Application Data

(60) Provisional application No. 62/690,117, filed on Jun. 26, 2018, provisional application No. 62/676,673, filed on May 25, 2018.

(51) Int. Cl.
A62B 9/02 (2006.01)
A62B 7/02 (2006.01)
B63C 11/24 (2006.01)
G01N 33/00 (2006.01)
A62B 27/00 (2006.01)

(52) U.S. Cl.
CPC .............. A62B 9/02 (2013.01); A62B 7/02 (2013.01); A62B 27/00 (2013.01); B63C 11/24 (2013.01); G01N 33/0006 (2013.01); G01N 33/0036 (2013.01)

(58) Field of Classification Search
CPC ......... B63C 11/00; B63C 11/02; B63C 11/12; B63C 11/18; B63C 11/22; B63C 11/2209; B63C 11/2227; B63C 11/2236; B63C 11/24; B63C 2011/026; B63C 2011/027; A62B 7/00; A62B 7/02; A62B 7/04; A62B 9/00; A62B 9/02; A62B 18/00; A62B 18/10; A62B 27/00
See application file for complete search history.

(56) References Cited

U.S. PATENT DOCUMENTS 3,727,626 A * 4/1973 Kanwisher .............. B63C 11/22
128/204.22
4,939,647 A * 7/1990 Clough ................... B63C 11/24
128/204.22
(Continued)

FOREIGN PATENT DOCUMENTS

GB 2404593 A 2/2005
WO 2005107390 A2 11/2005

Primary Examiner — Colin W Stuart
(74) Attorney, Agent, or Firm — MacMillan, Sobanski & Todd, LLC

(57) ABSTRACT

A rebreather apparatus includes at least one pressurized container of oxygen, at least one pressurized container of a diluting gas, and at least one valve to supply the oxygen and diluting gas to a rebreathing loop. The valve is controlled by a signal from at least one oxygen sensor, wherein the oxygen and diluting gas combine to form a breathing gas that is circulated by the rebreathing loop. At least one container of calibrating gas stores the calibrating gas at ambient pressure and temperature. At least one valve is connected to the at least one oxygen sensor presenting the calibrating gas to the oxygen sensor during calibration of the oxygen sensor and presenting the breathing gas to the oxygen sensor at all other times.

6 Claims, 14 Drawing Sheets

(56) References Cited

U.S. PATENT DOCUMENTS

| | | | |
|---|---|---|---|
| 6,712,071 B1* | 3/2004 | Parker | B63C 11/24 |
| | | | 128/203.14 |
| 8,424,522 B2 | 4/2013 | Sieber | |
| 2003/0188744 A1 | 10/2003 | Deas et al. | |
| 2007/0215157 A1* | 9/2007 | Straw | A62B 9/006 |
| | | | 128/205.12 |
| 2010/0313887 A1* | 12/2010 | Sieber | B63C 11/32 |
| | | | 128/204.22 |
| 2011/0041848 A1* | 2/2011 | Stone | B63C 11/12 |
| | | | 128/203.14 |

* cited by examiner

Outer barrel is 60mm inside inner barrel is 49.5mm outside or best clearance fit. Wall thickness as needed 18x1 thread is 6.5mm deep. All holes and slot on center.

A-A (1:1)

A-A (1:1)

A-A (1:1)

OXYGEN SENSOR CALIBRATION FOR REBREATHER

CROSS-REFERENCE TO RELATED APPLICATIONS

This application claims the benefit of U.S. Provisional Application Nos. 62/676,673, filed May 25, 2018 and 62/690,117, filed Jun. 26, 2018. The disclosures of both of these applications are incorporated herein by reference.

BACKGROUND OF THE INVENTION

The present disclosure relates to apparatuses and methods for calibrating an oxygen cell or cells of a respiration device, including a rebreather.

Open-circuit diving apparatuses are characterized by a supply cylinder of breathing gas, which cylinder is filled with compressed air or another mix of breathing gas, and a one level or two-level pressure reducer, which reduces the pressure of the gas in the cylinder to ambient pressure. The exhaled air is emitted in the water, and only a small fraction of the oxygen in the breathing gas is used. Thus, at the water surface, about 3% of inhaled gas is used (25 liter breathing minute volume, 0.8 liter used oxygen, at rest), and at a further depth, for example 20 m, this value drops to ⅓ of such use or 1% inhaled gas, due to the 2 bar increased ambient pressure. Consequently, for a diving operation at 20 m, 100 times more breathing gas must be carried along than what is actually used.

In order to avoid the low efficiency of breathing gas usage that is inherent in open-circuit diving apparatuses (SCUBA, compressed air diving apparatuses), semi-closed circuit and fully-closed circuit rebreathers are employed. In these apparatuses, breathing is done in a loop. Exhaled air in these apparatuses is cleaned from carbon dioxide by means of a carbon dioxide absorber and is again enriched with oxygen. Such apparatuses are further characterized by a one-part or two-part counter-lung, which can receive the exhaled gas volumes. With rebreathers, the efficiency regarding gas usage can be improved to up to 100%.

The present disclosure concerns such semi-closed circuit and fully-closed circuit rebreathers and a method for operating these devices.

Whereas users of open-circuit diving apparatuses normally inhale a gas with breathable oxygen content, in semi-closed circuit rebreathers, the oxygen partial pressure ("pO2") in the loop is based on the supplied amount of gas and the metabolism of the diver and is kept at a defined level in electronically controlled, fully closed circuit rebreathers by a control circuit (see GB 2404593 A, US 2003188744 A1, and WO 2005/107390 A2). In manually controlled, fully-closed circuit rebreathers, the oxygen supply is manually set by the diver and, therefore, the pO2 is manually adjusted. The pO2 of the breathing gas must be within certain defined limits to be breathable. Commonly, 0.16 bar is considered a lower limit and 1.6 bar an upper limit A pO2 below or above these limits is considered life threatening. Thus, constant monitoring of the pO2 is necessary for rebreathers. Fully closed circuit rebreathers require pO2 sensors ("oxygen sensors" or "oxygen sensor cells") for manually or electronically controlled adjustment of pO2 in a rebreathing loop. Normally, electro-chemical galvanic or fluorescent dye sensors are employed as pO2 sensors, which may be calibrated with air or 100% oxygen gas before a diving operation at the water surface.

Historically, the calibration of oxygen sensors required the flushing of the breathing loop with a calibration gas of a sufficient quantity to displace the breathing gas at an oxygen sensor cell membrane face. This could be done with multiple oxygen sensors installed in the rebreathing loop or to a single oxygen sensor cell by placing an injector nozzle of the calibration gas close to the cell membrane of each cell.

In most traditional multi-cell rebreathers, the rebreathing loop is opened to ambient pressure at the earth's surface prior to operation. The rebreathing loop is then flooded with oxygen until the oxygen sensors stop increasing in current. At this point, the assumption is that the oxygen at the face of each sensor is at its maximum concentration and at ambient pressure. The controller knows the ambient pressure outside of the breathing loop, as well as the temperature and concentration of the calibration oxygen. When the oxygen sensor cells are stable at maximum current, the controller makes a calibration calculation for each sensor and stores this information. During operation, the controller compares the sensors to each of the other sensors and uses the sensors which are most in agreement to assume accuracy. This may also be referred to as a vote made by the oxygen sensors. Typical rebreathers use three sensors, but some use up to seven sensors.

A significant disadvantage to this operation method is the potential failure of more than one sensor, resulting in the controller selecting the failing sensors as accurate and the loss of calibration of all the sensors over time and changes in pressure, temperature, and moisture. Since the controller can only compare the sensors to each other, any calibration error which affects all the sensors will not be recognized by the controller.

A desired solution for rebreather apparatus, and the oxygen sensor(s) of those apparatuses, is the ability to accurately calibrate or re-calibrate oxygen sensor(s) during normal operation. While some rebreathers involve a method to test the calibration during operation by flooding the breathing loop with oxygen or another known gas, this does not result in a sufficiently accurate reading to re-calibrate the controller. This test may also result in flooding the breathing loop with a gas mix that is harmful or fatal at operating pressures and demands extreme training for such a procedure.

U.S. Pat. No. 8,424,522 suggests a method to enable the calibration and re-calibration of a rebreather during operation. The method disclosed suggests injecting oxygen or a known diluent directly onto the membrane face of an oxygen sensor cell. The method teaches that sufficient calibration gas is flushed onto the face of the oxygen sensor cell to displace the breathing gas in the breathing loop. This calibration gas is continuously flushed onto the face of the oxygen sensor until a calibration or re-calibration is trusted and achieved. The patent does not teach or disclose the resultant negative effect of adding the calibration gas to the breathing gas mix or of the significant cooling effect of expanding compressed calibration gas directly onto the oxygen sensor cell membrane. While the patent also discloses that this method can be used for more than one oxygen sensor cell, it requires separate and individual gas injectors for each cell.

SUMMARY OF THE INVENTION

The present disclosure teaches a method of calibrating and re-calibrating a respiration device or rebreather during operation while avoiding the complications and negative effects of the above disclosed apparatuses and methods in the prior art. The present disclosure incorporates a novel method of using a separate shielding container, at ambient pressure and temperature, of a small quantity of calibration gas. The oxygen sensor or sensors are then periodically exposed to this high concentration of calibration gas while being mostly separated from the breathing gas in the rebreathing loop. This method does not require the flushing of the oxygen sensor cell membrane with calibration gas or the displacement of large volumes of breathing gas from the cell membrane by the calibration gas. The benefits include the use of very little calibration gas during the calibration, faster calibration as little breathing gas needs to first be displaced, no change in the breathing gas mix during calibration and no change in temperature of the oxygen sensor during calibration.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
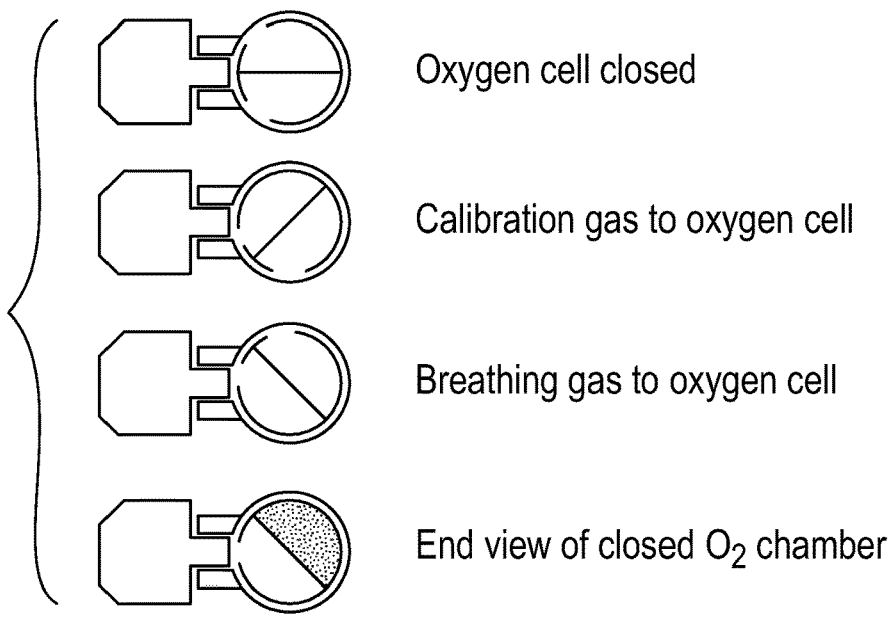
FIG. 1 illustrates several schematic diagrams of an oxygen sensor and the alternate positions of a barrel valve according to an embodiment of the present disclosure.

The present disclosure teaches the use of a small, mostly separate container of calibration gas kept at the same effective pressure and temperature as the breathing gas by a small fluid connection to the breathing gas. A valve, shutter, or other device changes the oxygen sensor input between the breathing gas in normal mode and the calibration gas during a calibration cycle. The exact valve or method of switching the oxygen sensor from gas to gas is not necessarily critical to the method. The current state of the art incorporates a single port for the oxygen sensor. However, this is not a technical limitation, and a dual port oxygen sensor could be used. In a single-port oxygen sensor, a rotating barrel, sliding barrel, rotating or sliding cap, or other valve could direct breathing gas or calibration gas to the oxygen sensor input. Using a multi-port oxygen sensor, a shutter or other valve could be inversely opened and closed to expose the gas inputs of the sensor to the breathing gas or to the calibration gas.

The present disclosure teaches a method of calibrating and re-calibrating a respiration device or rebreather during operation using either a single oxygen sensor or multiple oxygen sensors. The method is not limited by inclusion of multiple oxygen sensors. Multiple oxygen sensors could be mounted to the same or different valve systems and could use the same or different calibration gas chambers. For less critical applications, a single oxygen sensor could be used for re-calibration during operation and could detect sensor failure or sensor output variations from temperature, pressure, time, or moisture.

The present disclosure teaches a novel oxygen sensor having multiple gas ports fluidly connected to a single sensor device. Oxygen sensors used in respiration devices are designed to for high sensitivity and fast response to changes in oxygen partial pressure and operation in low temperature environments. The most commonly used technologies are electrochemical, as they excel in the above properties. However, other types of sensors, such as fluorescent dye sensors, may also be used. Current electrochemical and dye-based oxygen sensors have a gas permeable membrane usually made of expanded PTFE covering a single gas inlet port. The membrane is designed to allow the free exchange of gas through the port to and from the sensor. With electrochemical sensors, the membrane also retains the liquid electrolyte inside the sensor. The electrolyte absorbs and emits gas through the membrane due to Boyle's law of partial pressures. As the sensor electrolyte absorbs oxygen, the anode in the sensor oxidizes, and a current is produced between the anode and cathode in proportion to the oxygen partial pressure. With Fluorescent dye sensors, a dye substrate is mounted behind the PTFE membrane and exposed to the partial pressure of the gas. As the partial pressure of oxygen changes, the dye changes the fluorescent dwell after excitation with short durations of narrow wavelengths of light. In a novel method for calibrating oxygen sensors while in use, pure oxygen for calibration and the gas to be measured are each individually presented to the oxygen sensor membrane. It is advantageous to have a sensor with a least two ports, using a single or multiple membranes fluidly connected to the same sensor. Each gas can then be presented to each port by inverse valves, and the sensor will then absorb or dissipate oxygen based on the partial pressure of each gas. Since moisture on the surface of the sensor membrane slows the absorption of gas, it is advantageous to have the ports use the same membrane, but this is not necessary.

The present disclosure also teaches a novel valve for directing two gases alternately to the same port of a sensor. The valve is designed to allow the free flow of a breathing gas to access the sensor face while semi-enclosing a chamber in the other side of the valve for a calibration gas. During normal operation, a solenoid type injector valve periodically flows oxygen into the calibration chamber. The oxygen floods the mixing chamber, then flows out of a fluid connected opening between the calibration chamber and the breathing gas chamber, mixing with the breathing gas. During the calibration mode, the oxygen sensor face is exposed to the calibration chamber, rather than the breathing gas chamber. The calibration chamber is mostly oxygen, yet the injector valve cycles a small additional amount of oxygen into the calibration chamber to assure the chamber is at a high concentration of calibration gas. The fluid connected opening between the chambers assures the two chambers are always at the same pressure. The design passes breathing gas alongside the calibration gas chamber, effectively keeping the calibration gas at the same temperature as the breathing gas. In some design variations, the valve also has a third mode to close off the sensor to the gas of both chambers to starve the sensor of gas. This may prolong the useful life of the sensor.

The present disclosure teaches an embodiment where a novel well creates a calibration chamber. A Florescent Dye oxygen sensor is positioned on the well bottom, and a movable simple cover or shutter acting as a switch (calibration valve) may loosely cover or expose the well. The calibration valve is coupled to the top of the well in such a manner where the valve is movable to mostly block the opening of the well and prevent exposure of the sensor to the flow of breathing gas. Since a Florescent Dye oxygen sensor is less sensitive to temperature changes compared to other sensors, the use for this purpose is beneficial. A loosely covered well limits the sensor exposure to breathing gas, while an uncovered well further exposes the sensor to breathing gas. The well is configured for the injection of oxygen to a side of the sensor via an injector valve. The valve injector may be fluidly coupled to the external surface of the well by one or more fasteners or may be constrained in an adjacent well. Fluid access from the injector valve to the sensor side is provided by a path though the well wall tangent to the cross sectional edge of the calibration chamber. This path has a cross sectional area to at least facilitate gas injection to the sensor side. The well is further constructed to allow the gas to swirl up and out of the well following injection. In one instance, the gas sensor is disposed on the well floor such that a perimeter channel is formed between the gas sensor and the well wall. Additionally, the gas sensor and calibration chamber can both be dimensionally sized such that the gas sensor is received by the calibration chamber. A slight increase in partial pressure oxygen ("pO2") reading briefly results after each injection of oxygen as the gas swirls up and out of the well chamber. This slight increase is an indication that the injector valve and sensor are working. Since the indication can occur while a sensor is exposed to breathing gas, it is advantageous to use side injection. Swirling of gas up and out of the well is advantageous since the gas is warmed, and the cooling of the sensor is reduced.

In a novel method to determine whether injector valves and sensors are working during operation mode, a Florescent Dye oxygen sensor is positioned in the well chamber. Pure oxygen is injected to the side of the sensor during the operation mode. The oxygen is then allowed to swirl up and out of the uncovered chamber, producing a brief increase in pO2 indicating that the injector and sensor are working.

The present disclosure teaches a variety of actuators that may activate the calibration valve. The calibration valve actuators can be pneumatic, solenoid, and shape memory alloy (SMA) actuators. In one embodiment, the calibration valve may be relationally located such that the open end of the well is entirely covered during calibration mode. Since the SMA torsion wires can be the axis shaft of each shutter, each shutter may be independent of the others. Since the shutters may be independent and have no bearing or contact surface, the failure of a shutter would not materially affect the outcome of operation or calibration mode. The wires may be attached on each end extending between to the two rails (a circuit board). The rails may be conductive and are generally located opposite one another. Each shutter vane is attached to the middle portion of the wire. At stasis, the vanes are generally perpendicular in relation to the well face due to the resting shape of the wire. A current is passed through the wire, heating it. The heating of the wire generates torsion causing the wire to twist and rotate the shutter vane ninety degrees toward the well face. Upon removal of the current, the wire cools and returns the shutter vane to a generally perpendicular open position in relation to the well.

FIG. 1 discloses an embodiment of an oxygen sensor and barrel valve, where alternate positions of the barrel valve are depicted. In a first position, the oxygen sensor cell is closed from any gases. In a second position, the barrel valve is positioned in such a way that calibration gas is presented to the oxygen sensor cell. In a third position, the barrel valve is positioned in such a way that breathing gas of a rebreathing loop is presented to the oxygen sensor cell for monitoring of the pO2 levels of the breathing gas.

Figure 2:
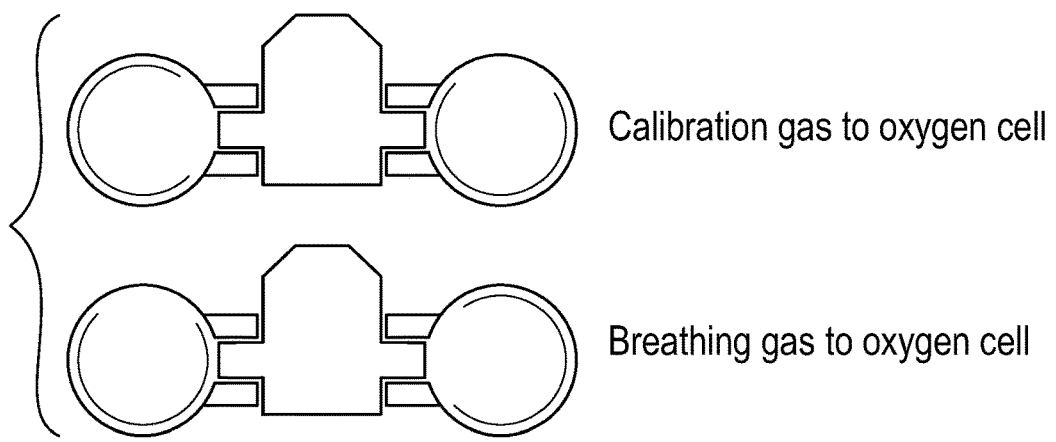
FIG. 2 illustrates several schematic diagrams of a novel oxygen sensor according to an embodiment of the present disclosure.

FIG. 2 discloses an embodiment of an oxygen sensor cell comprising two barrel valves on opposing ends of the oxygen sensor cell, where one barrel valve is connected to a calibration gas container and the other barrel valve is connected to a rebreathing loop. During calibration, the barrel valve connected to the calibration gas container is positioned in such a way such that calibration gas is presented to the oxygen sensor cell, while the barrel valve connected to the rebreathing loop is positioned such that the breathing gas is closed to the oxygen sensor. When the oxygen sensor is measuring the pO2 of the breathing gas, the barrel valve connected to the calibration gas container is positioned in such a way such that the calibration gas is closed to the oxygen sensor cell, while the barrel valve connected to the rebreathing loop is positioned such that breathing gas is presented to the oxygen sensor.

Figure 3:
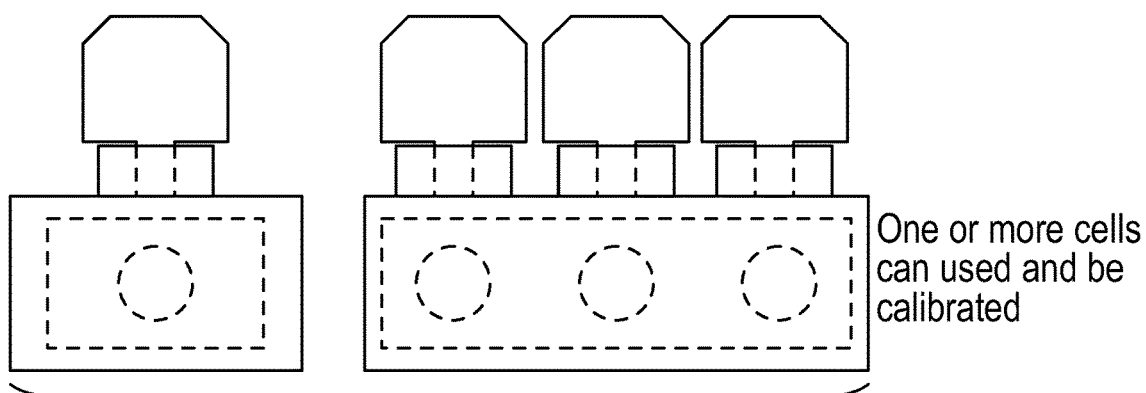
FIG. 3 is a schematic diagram of a one or multiple oxygen sensor configuration according to an embodiment of the present disclosure.

FIG. 3 discloses two embodiments of the present disclosure. A first diagram depicts a single oxygen sensor embodiment according to the present disclosure, and a second diagram depicts an embodiment with multiple oxygen sensors according to the present disclosure.

Figure 4:
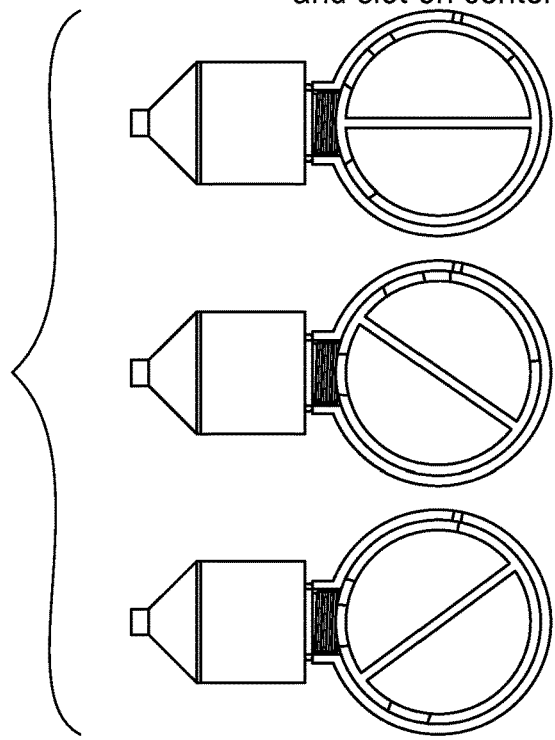
FIG. 4 is a schematic diagram of a barrel valve according to an embodiment of the present disclosure.

FIG. 4 discloses an embodiment of the barrel valve according to the present disclosure. The barrel valve is illustrated in alternate positions. In a first position, the valve closes off presentment of any gas through its port. In a second position, gas from a first chamber is presented through the port of the barrel valve, while a gas in a second chamber is closed off. In a third position, the gas in the second chamber is presented through the port of the barrel valve, while the gas in the first chamber is closed off.

Figure 5:
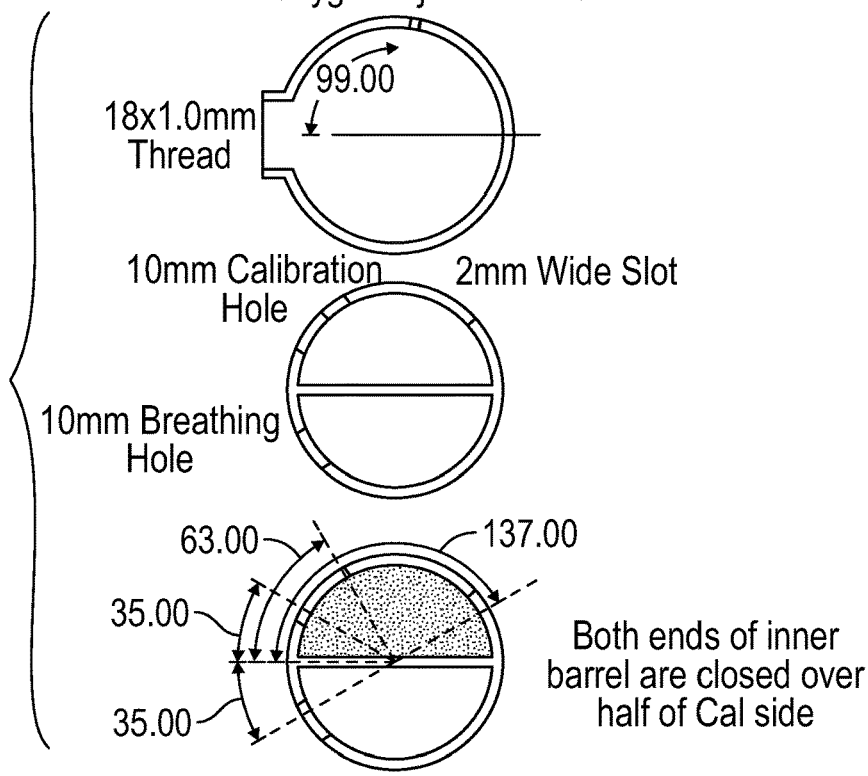
FIG. 5 is a schematic diagram of a barrel valve according to an embodiment of the present disclosure.

FIG. 5 depicts an embodiment of the barrel valve according to the present disclosure in more detail. FIG. 5 depicts an outer and inner barrel of the barrel valve, and holes in the walls of the outer and inner barrels allow the transfer of gases in the chambers of the inner barrel.

Figure 6:
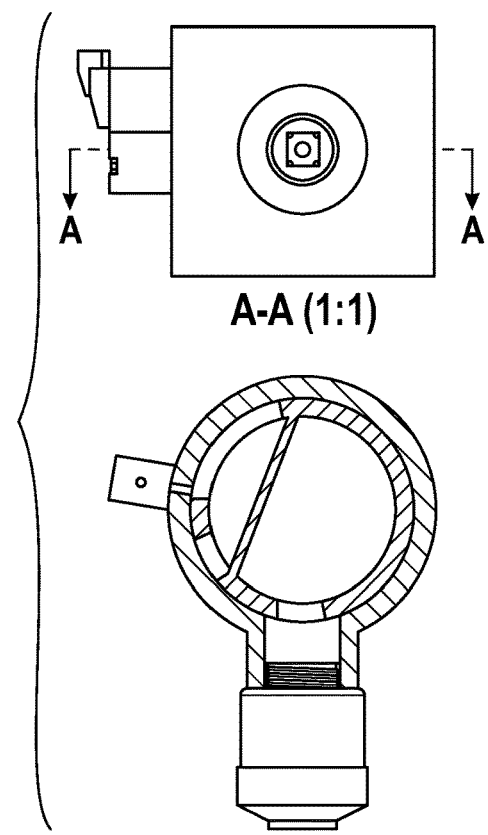
FIG. 6 is a cut-away diagram of a rotating barrel valve in the Operating position according to the present disclosure.
Figure 7:
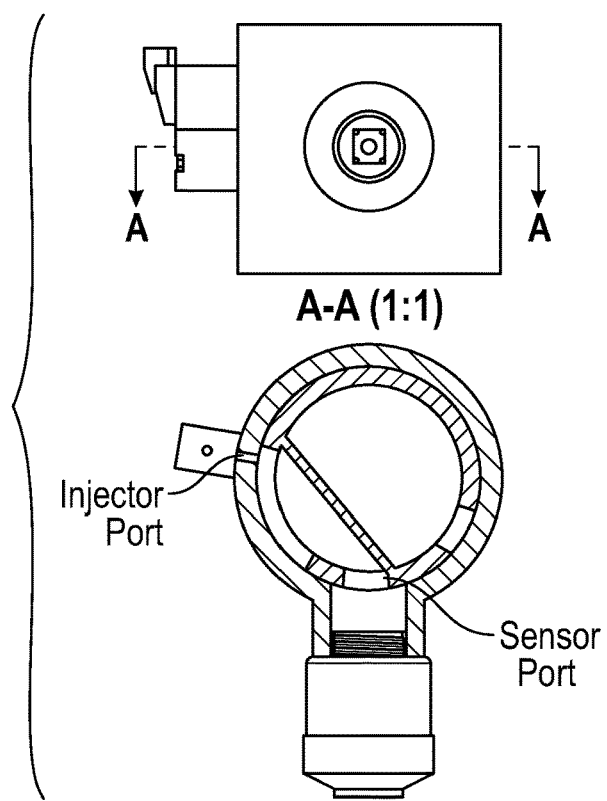
FIG. 7 is a cut-away diagram of a rotating barrel valve in the Calibration position according to the present disclosure.

FIGS. 6 and 7 depict an embodiment of a barrel valve according to the present disclosure, wherein an inner barrel of the barrel valve is divided into two sections, namely, a chamber for presenting the calibration gas to an oxygen sensor and a channel connected to a rebreathing loop for presenting a breathing gas in the rebreathing loop to the oxygen sensor.

Figure 8:
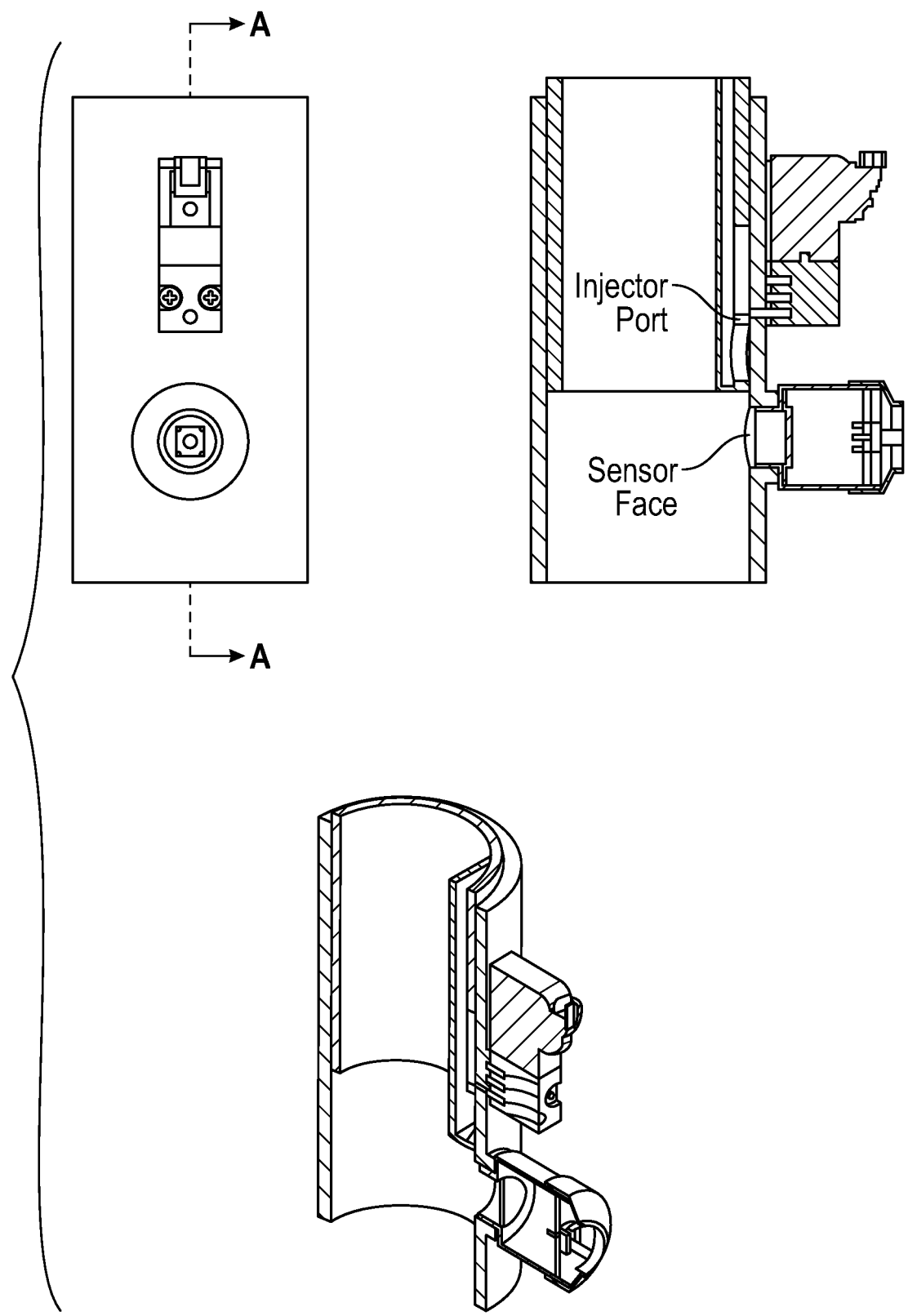
FIG. 8 is a cut-away diagram of a slide barrel valve in the Operating position according to the present disclosure.
Figure 9:
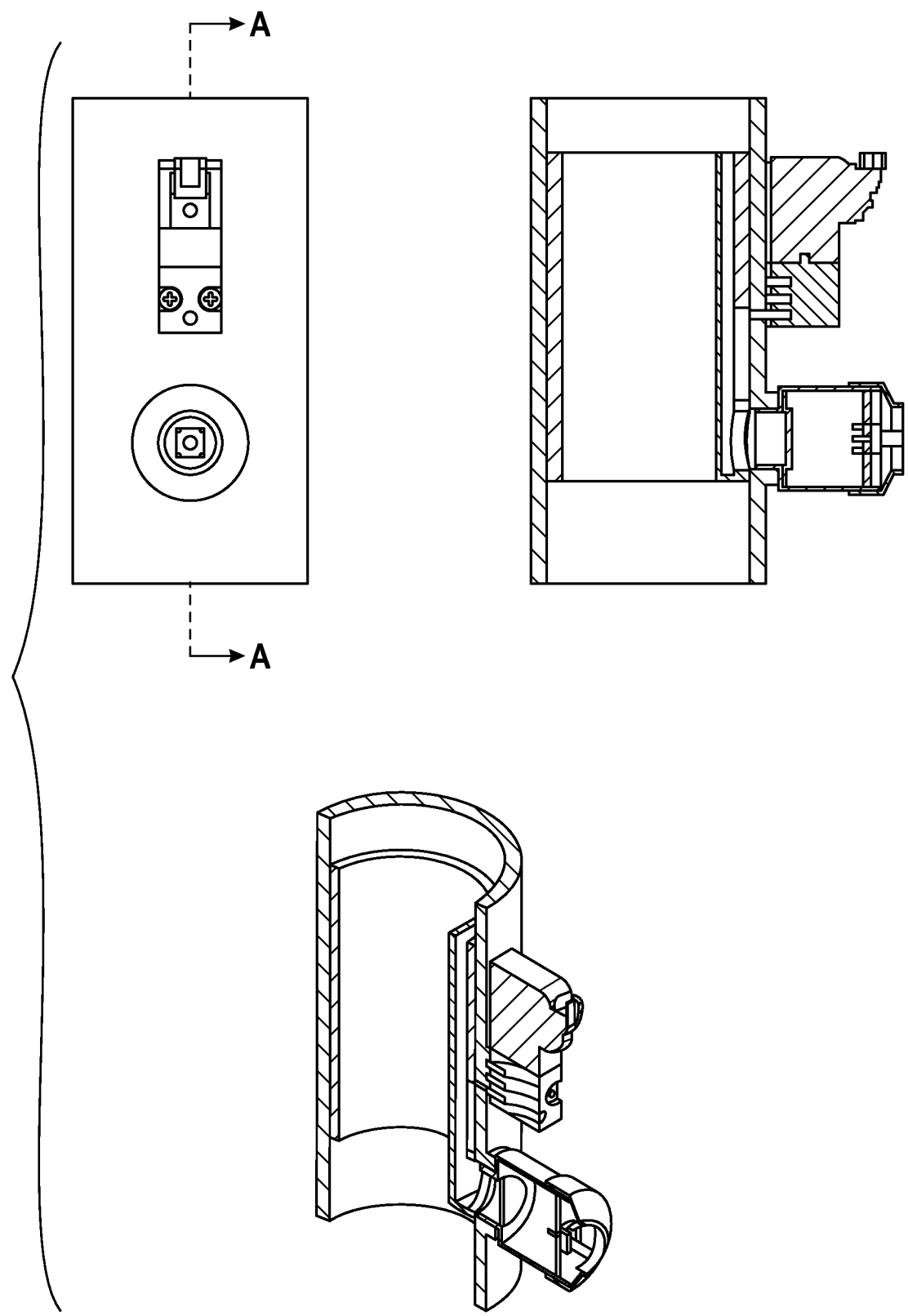
FIG. 9 is a cut-away diagram of a slide barrel valve in the Calibration position according to the present disclosure.

FIGS. 8 and 9 depict an embodiment of a sliding barrel valve according to the present disclosure, wherein an inner barrel of the barrel valve is divided into two sections, namely, a chamber for presenting the calibration gas to an oxygen sensor and a channel connected to a rebreathing loop for presenting a breathing gas in the rebreathing loop to the oxygen sensor.

Figure 10:
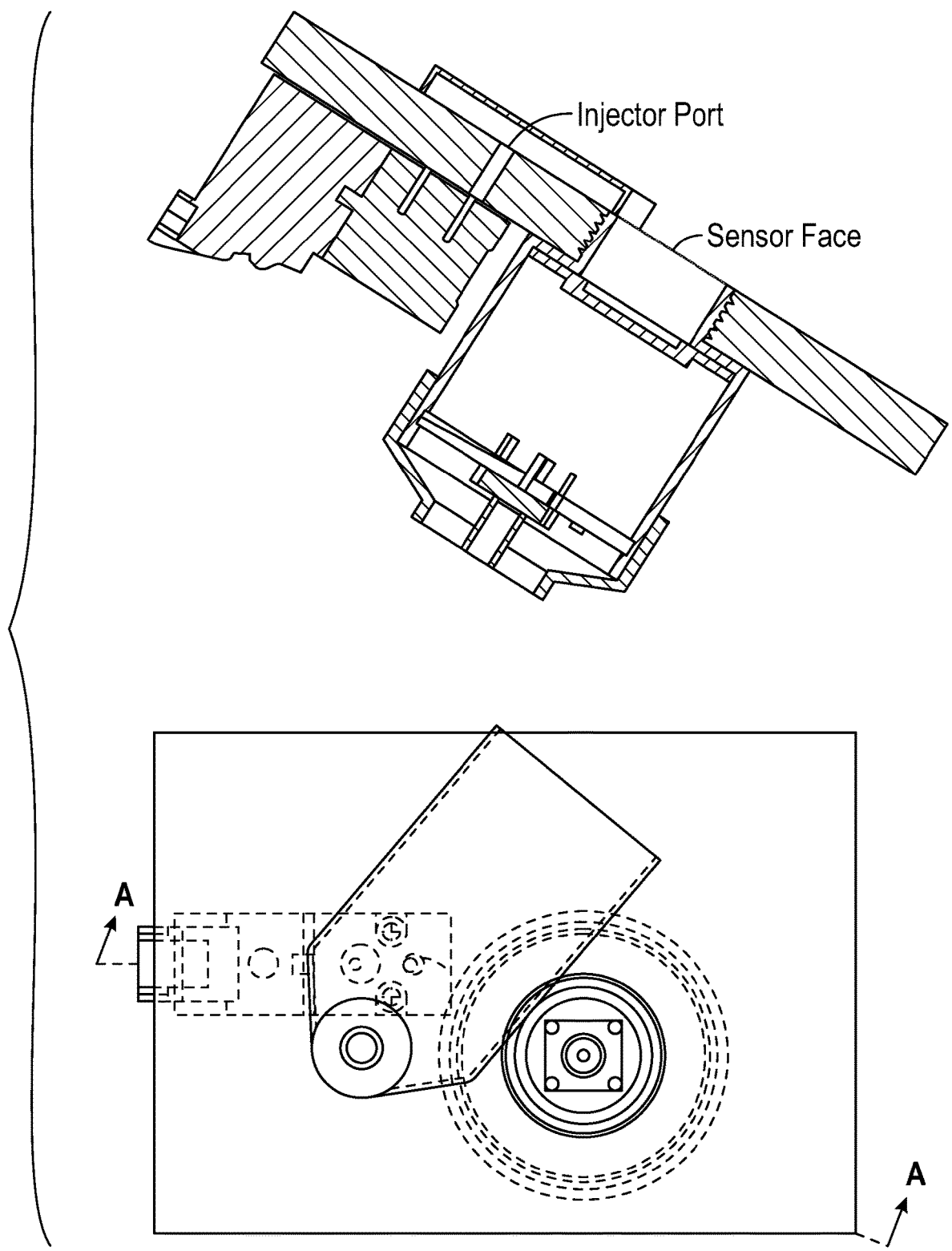
FIG. 10 is a cut-away diagram of a swing cap chamber valve in the Operating position according to the present disclosure.
Figure 11:
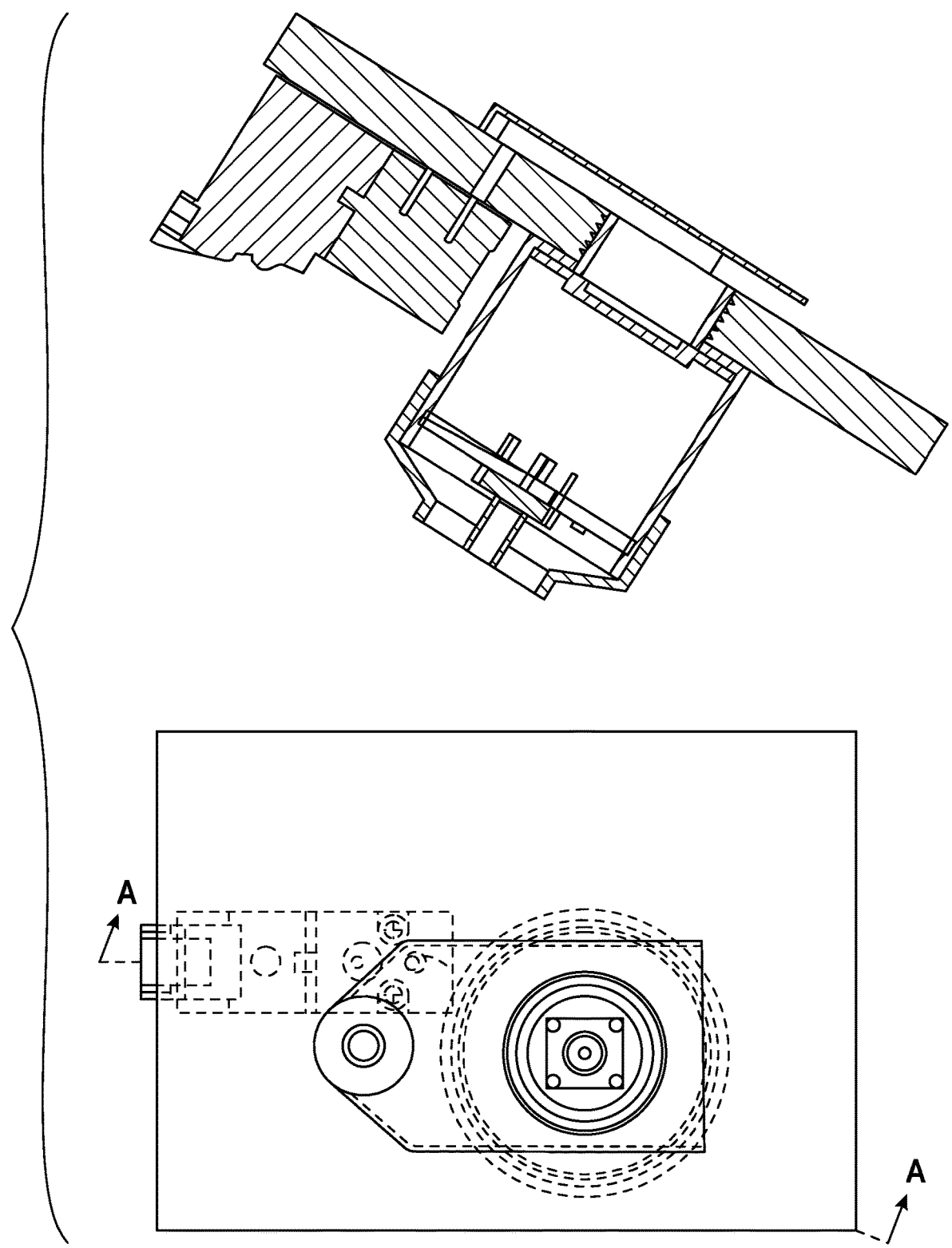
FIG. 11 is a cut-away diagram of a swing cap chamber valve in the Calibration position according to the present disclosure.

FIGS. 10 and 11 depict an embodiment of a swing cap valve according to the present disclosure, wherein a movable shelled cap creates a chamber for the calibration gas. This cap rotates to the sensor to present the calibration gas to an oxygen sensor.

Figure 12:
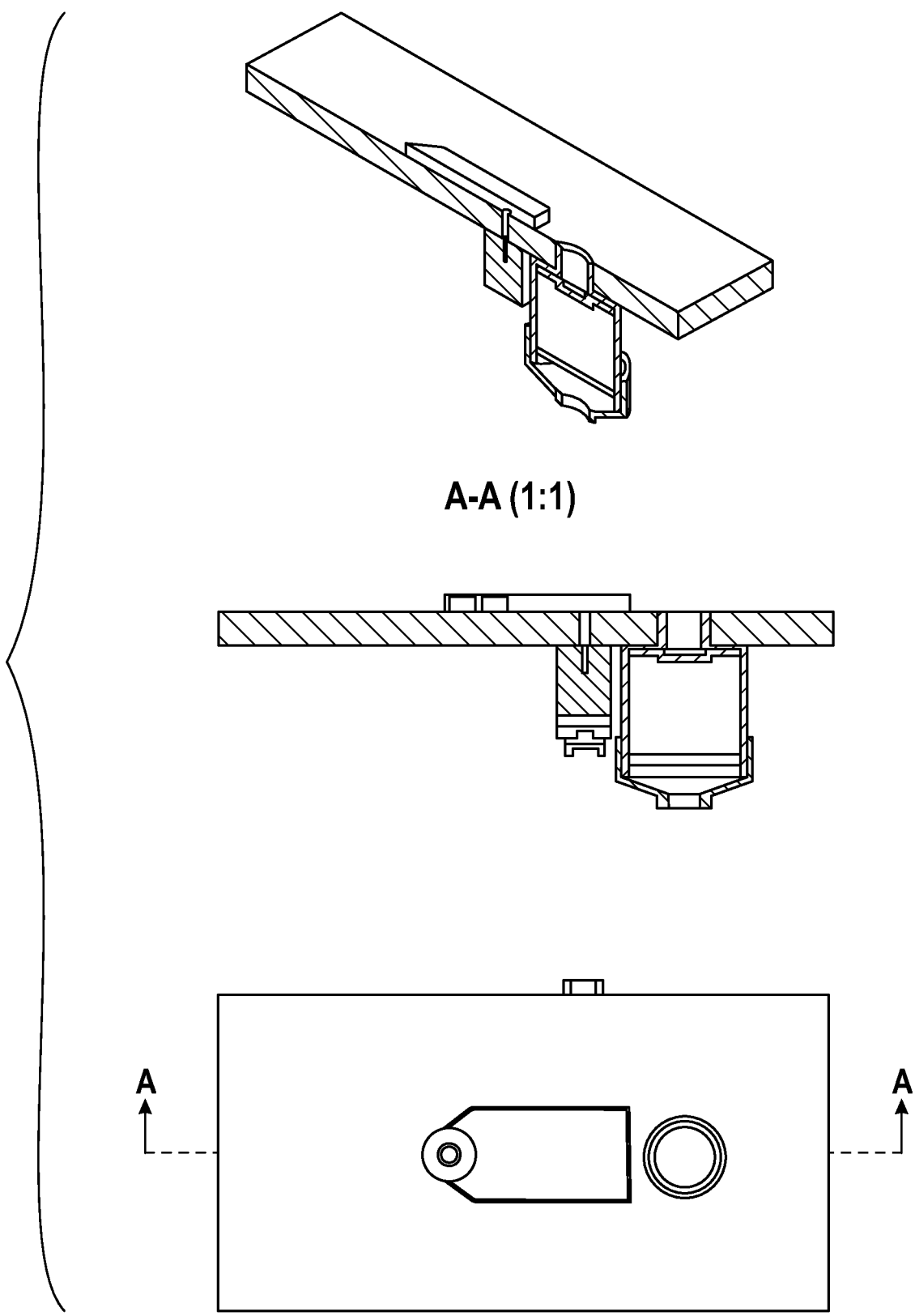
FIG. 12 is a cut-away diagram of a slide cap chamber valve in the Operating position according to the present disclosure.
Figure 13:
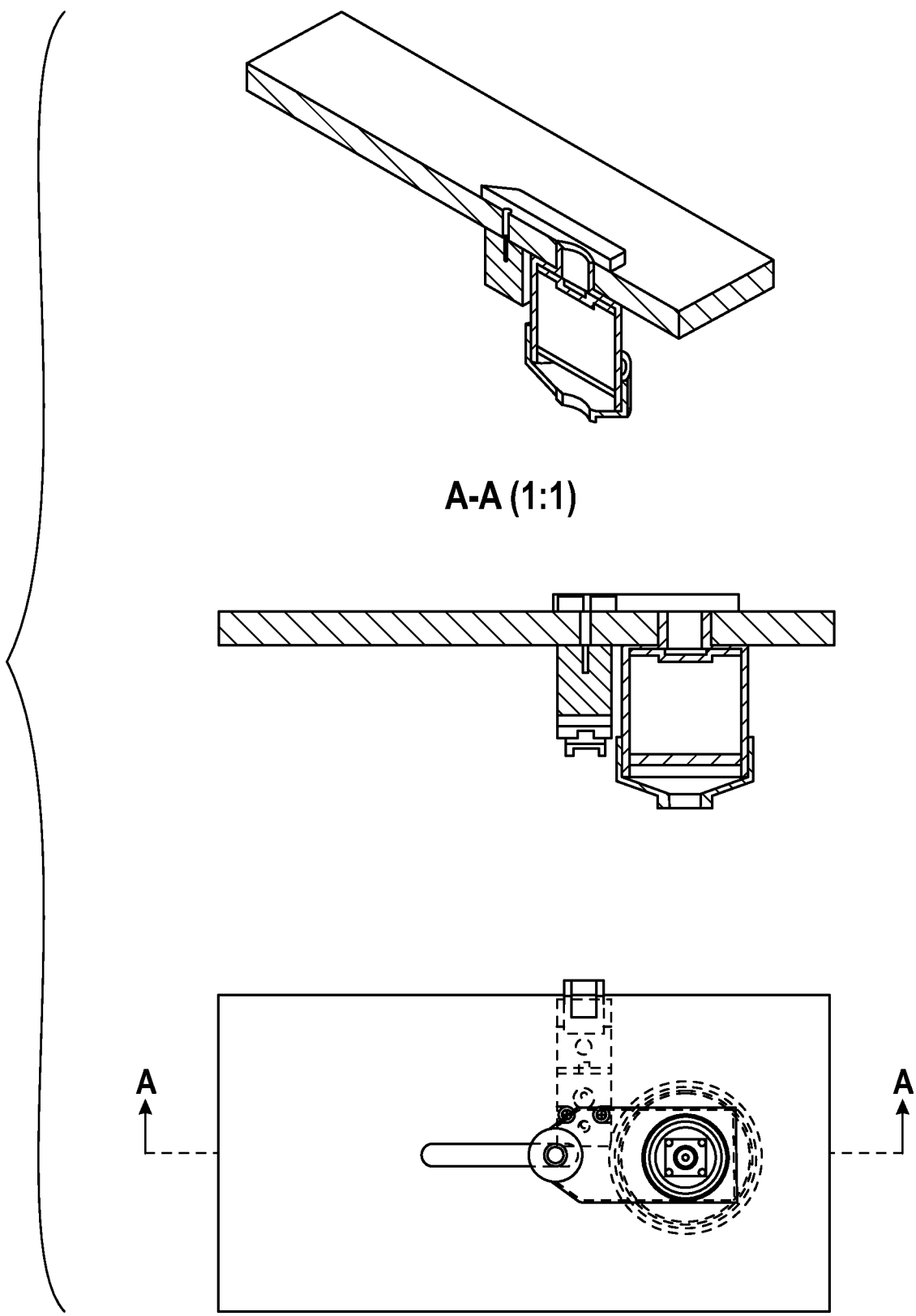
FIG. 13 is a cut-away diagram of a slide cap chamber valve in the Calibration position according to the present disclosure.

FIGS. 12 and 13 depict an embodiment of a sliding cap valve according to the present disclosures wherein a movable shelled cap creates a chamber for the calibration gas. This cap slides towards the sensor to present the calibration gas to an oxygen sensor.

Figure 14:
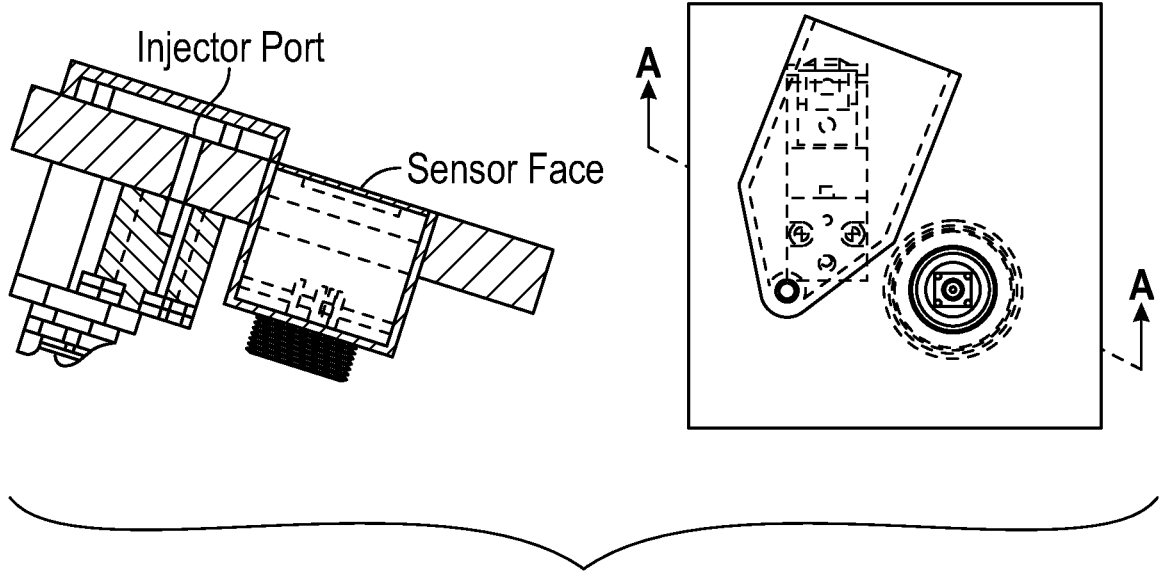
FIG. 14 is a cut-away diagram of a swing cap chamber valve with a dye sensor in the Operating position according to the present disclosure.
Figure 15:
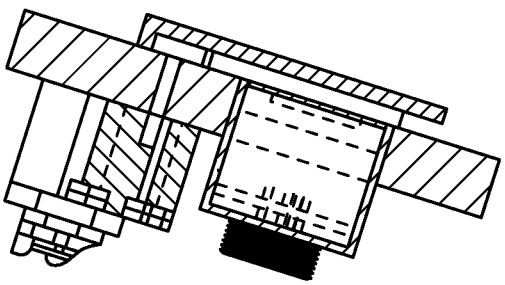
FIG. 15 is a cut-away diagram of a swing cap chamber valve with a dye sensor in the Calibration position according to the present disclosure.
Figure 15:
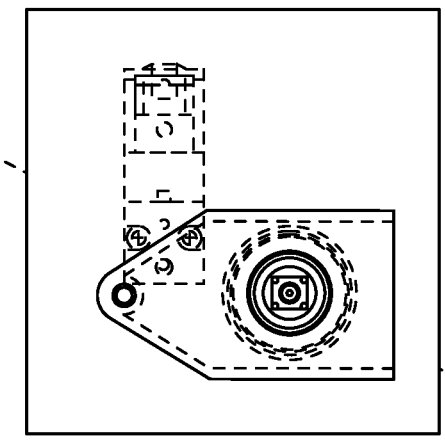

FIGS. 14 and 15 depict an embodiment of a swing cap valve according to the present disclosure, wherein a movable shelled cap creates a chamber for the calibration gas. This cap slides towards the sensor to present the calibration gas to a fluorescent dye oxygen sensor.

Figure 16:
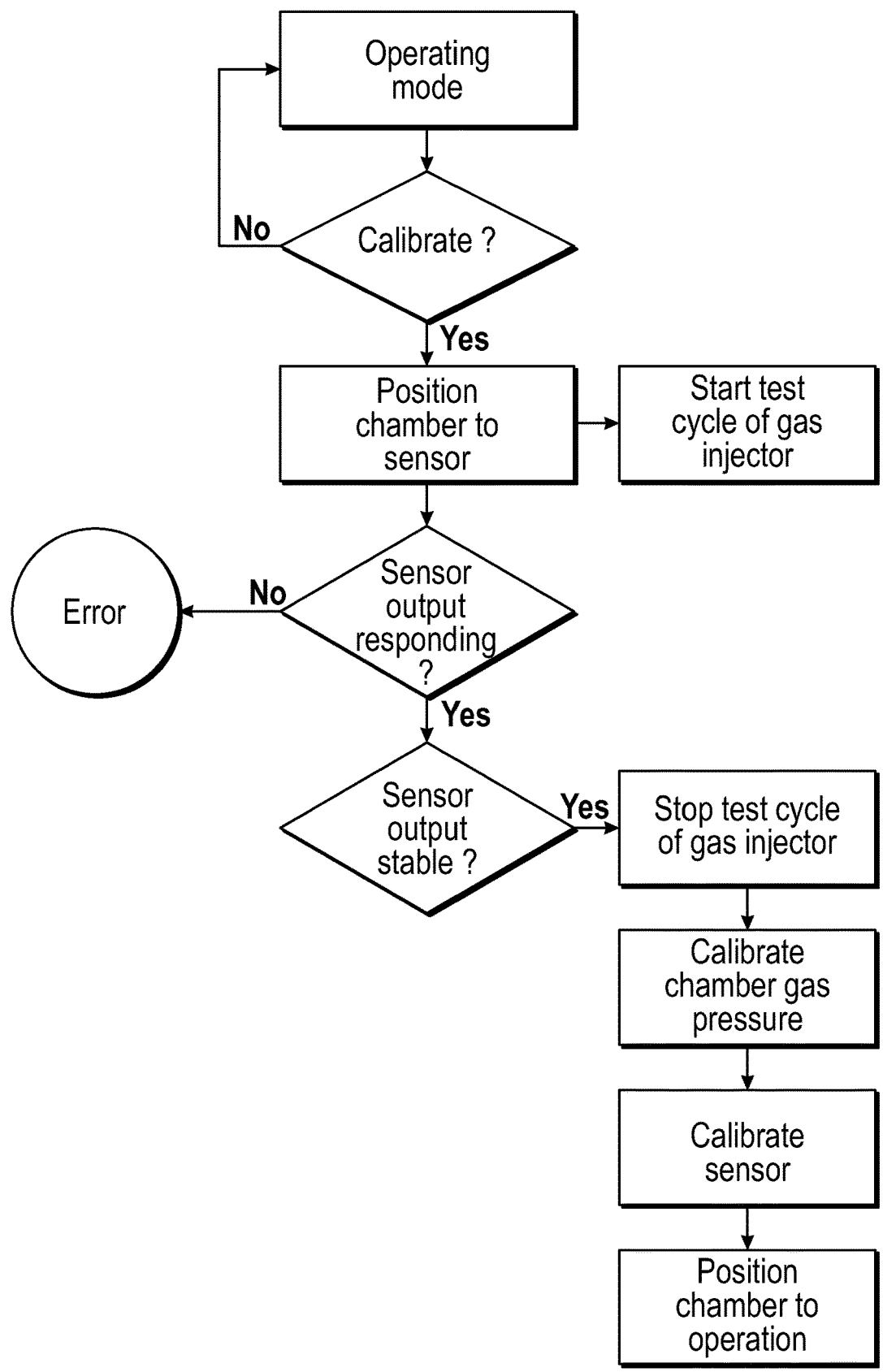
FIG. 16 is a flow diagram of one method of calibration according to the present disclosure.
Figure 17:
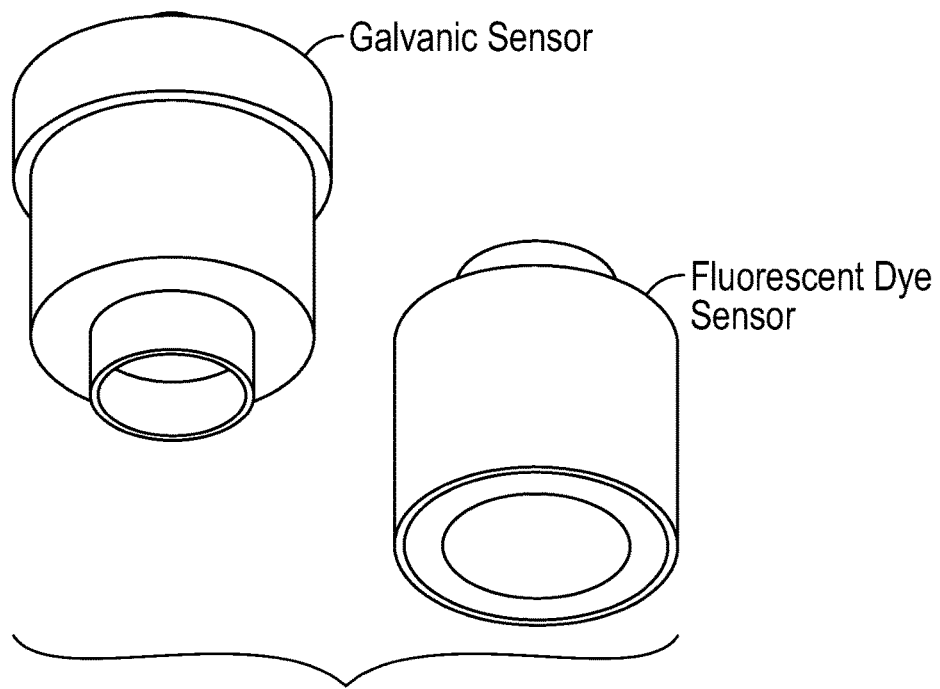
FIG. 17 shows two sensor types, namely, a Galvanic Sensor and a Fluorescent Dye Sensor.

FIG. 16 depicts an flow chart of one method of calibrating one or more sensors using the calibration chamber. When calibration is desired, the valve is positioned expose the oxygen sensor to the calibration gas chamber. The injector valve cycles to assure the concentration of calibration gas inside the calibration chamber. If the sensor records no change in output, a potential error is processed. When the sensor has a stable output, the cycling of the injector valve stops, the pressure in the chamber is calculated, the sensors are calibrated, and the valve is returned to the operating position. Once the sensor output is stable, the oxygen injector the valve can be returned to the operating mode. It is not necessary to calculate the pressure or calibrate the sensor prior to returning the valve and injector to normal operation.

Figure 18:
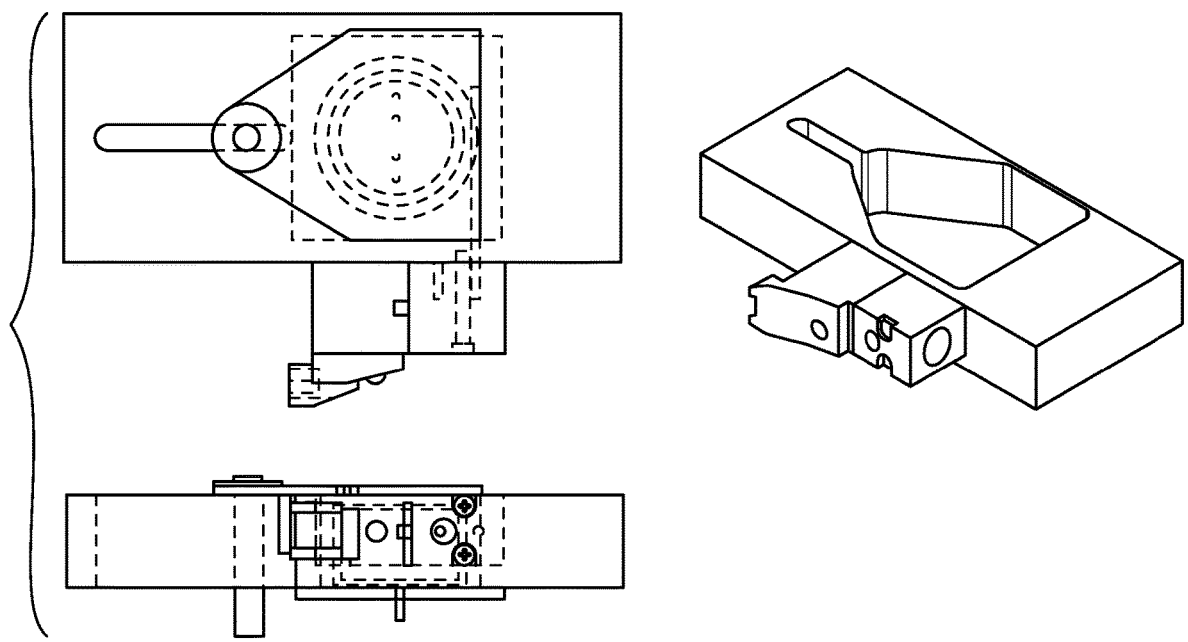
FIG. 18 is a transparent diagram of a slide cap valve well injector with a dye sensor in the Calibration position according to the present disclosure.
Figure 19:
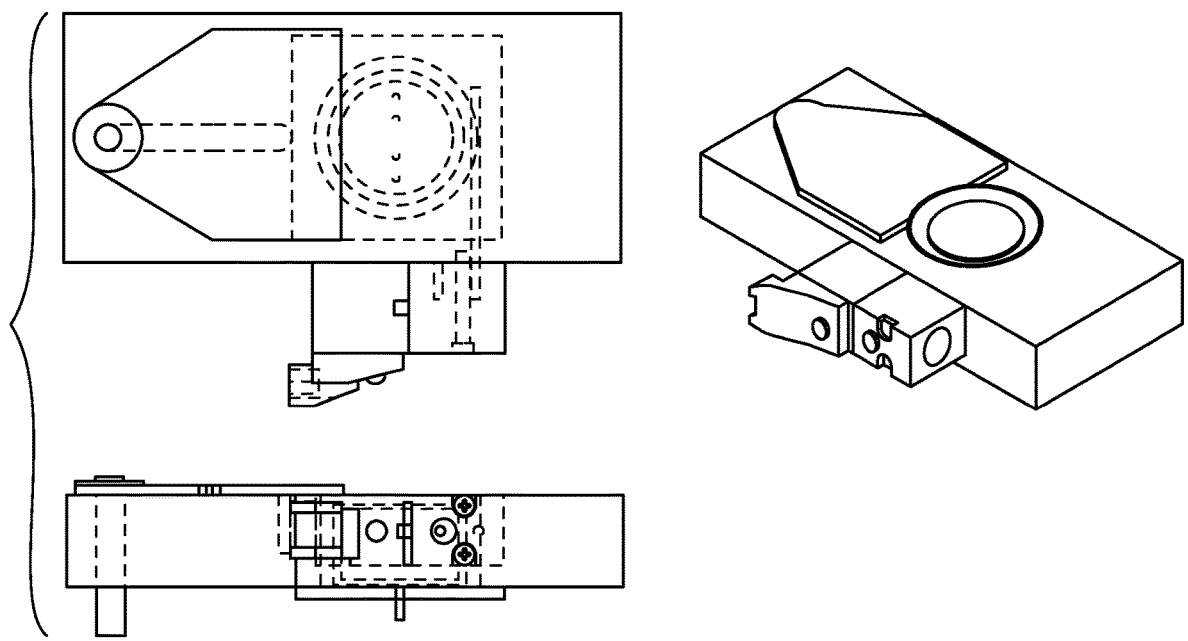
FIG. 19 is a transparent diagram of a slide cap valve well injector with a dye sensor in the Operating position according to the present disclosure.

FIGS. 18 and 19 depict an embodiment of a slide cap valve well injector with a dye sensor according to the present disclosure, wherein a movable cap covers the sensor. This cap slides toward the sensor to switch the sensor between gas types.

Figure 20:
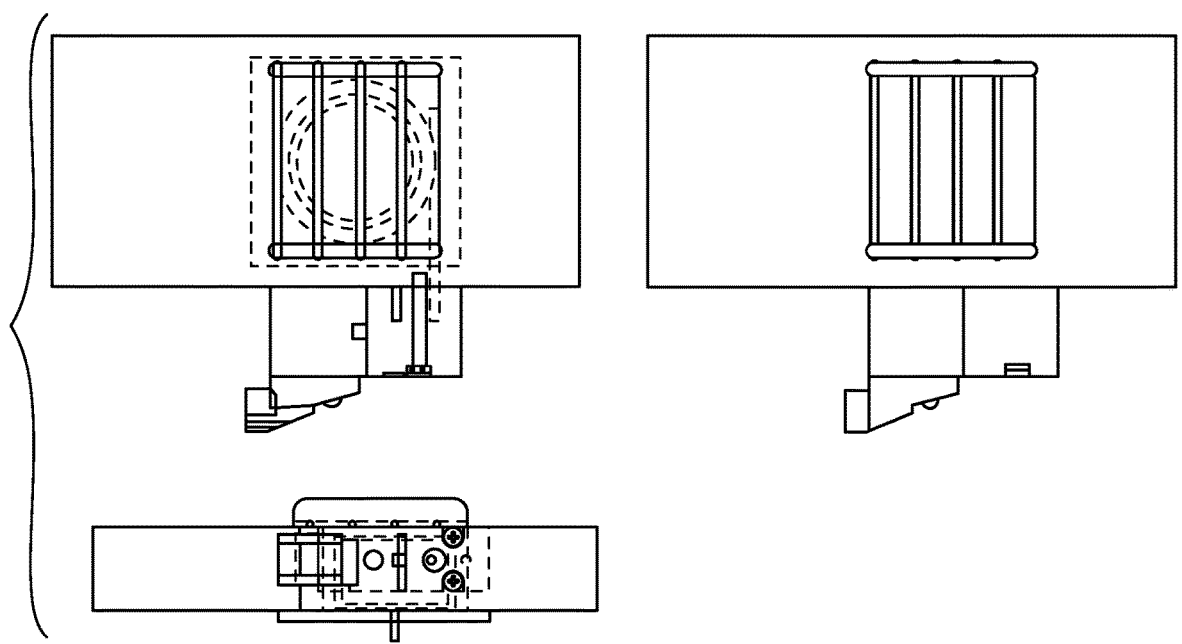
FIG. 20 is a transparent diagram of a shutter cap valve well injector with a dye sensor in the Calibration position according to the present disclosure.
Figure 21:
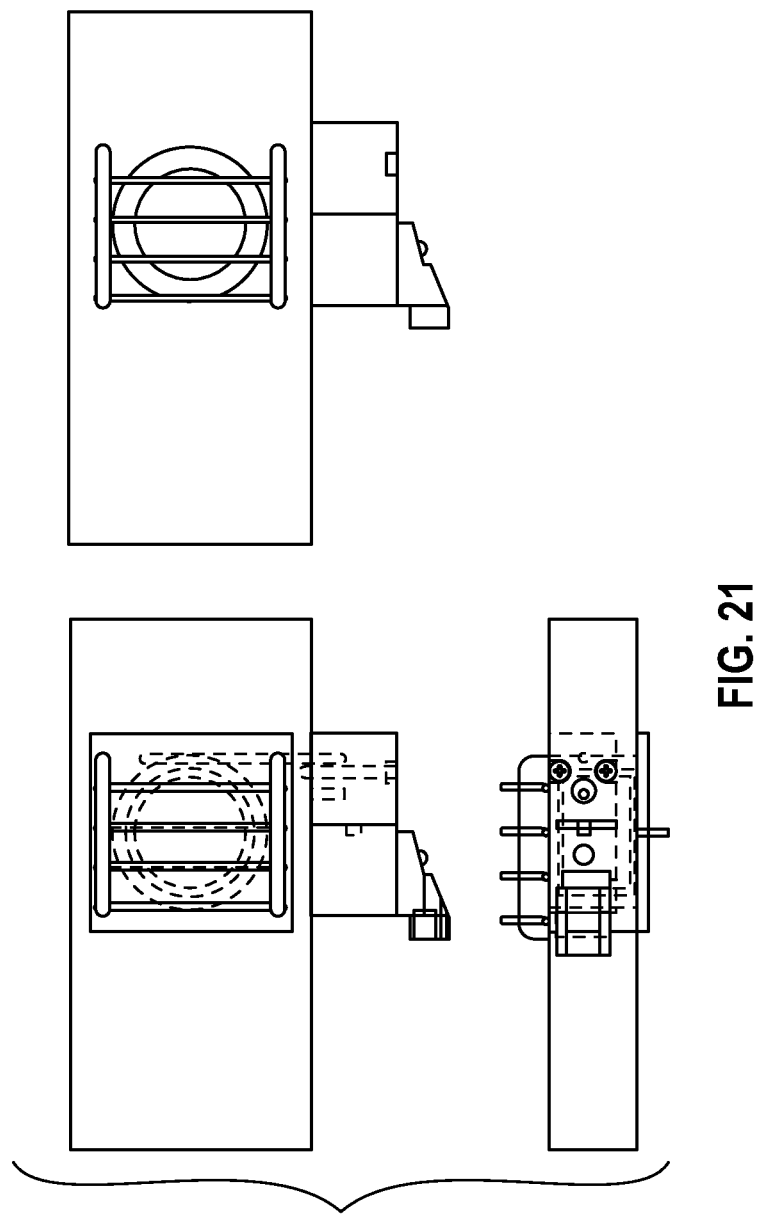
FIG. 21 is a transparent diagram of a shutter cap valve well injector with a dye sensor in the Operating position according to the present disclosure.

FIGS. 20 and 21 depict an embodiment of a shutter cap valve well injector with a dye sensor according to the present disclosure, wherein a movable slide covers the sensor. This cap rotates toward the sensor to switch the sensor between gas types.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A rebreather apparatus comprising:
   at least one pressurized container of oxygen;
   at least one pressurized container of a diluting gas;
   at least one supply valve to supply the oxygen and diluting gas to a rebreathing loop, the at least one supply valve being controlled by a signal from at least one oxygen sensor, wherein the oxygen and diluting gas combine to form a breathing gas that is circulated by the rebreathing loop;
   at least one container of calibrating gas storing the calibrating gas at ambient pressure and temperature; and
   at least one sensor valve connected to the at least one oxygen sensor presenting the calibrating gas to the at least one oxygen sensor during calibration of the at least one oxygen sensor and presenting the breathing gas to the at least one oxygen sensor at all other times.

2. A rebreather apparatus according to claim 1, wherein the at least one sensor valve is a rotating barrel valve.

3. A rebreather apparatus according to claim 2, wherein the at least one rotating barrel valve further includes a calibration chamber and a breathing gas chamber, wherein the calibration chamber is connected to the at least one container of calibrating gas, the breathing gas chamber is connected to the rebreathing loop, and the at least one rotating barrel valve rotates to present the calibration chamber to the oxygen sensor during calibration of the at least one oxygen sensor and rotates to present the breathing gas chamber to the oxygen sensor at all other times, allowing the at least one oxygen sensor to measure oxygen in the breathing gas during operation of the rebreather apparatus.

4. A rebreather apparatus according to claim 1, wherein the at least one sensor valve is a sliding barrel valve.

5. A rebreather apparatus according to claim 1, wherein the at least one sensor valve is a sliding cap valve.

6. A method of calibrating a rebreather apparatus including at least one pressurized container of oxygen; at least one pressurized container of diluting gas; at least one supply valve supplying the oxygen and diluting gas to a rebreathing loop of the rebreather apparatus, the at least one supply valve being controlled by a signal from at least one oxygen sensor, wherein the oxygen and diluting gas combine to form a breathing gas that is circulated by the rebreathing loop; at least one container of calibrating gas storing the calibrating gas at ambient pressure and temperature; at least one rotating barrel valve connected to the at least one oxygen sensor; wherein the at least one rotating barrel valve comprises a calibration chamber and a breathing gas chamber, further wherein the calibration chamber is connected to the at least one container of calibrating gas and the breathing gas chamber is connected to the rebreathing loop, wherein the method comprises the steps of:
   (a) initiating calibration of the rebreather apparatus;
   (b) rotating the at least one barrel valve to present the calibration chamber to the at least one oxygen sensor;
   (c) measuring the oxygen in the calibration gas by the at least one oxygen sensor for calibration; and (d) rotating the at least one barrel valve to present the breathing gas chamber to the at least one oxygen sensor to measure the oxygen in the breathing gas.

\* \* \* \* \*